(12) United States Patent
Egger

(10) Patent No.: US 8,045,172 B2
(45) Date of Patent: Oct. 25, 2011

(54) METHOD AND APPARATUS FOR DETERMINING THE CONCENTRATION OF A SUBSTANCE IN A LIQUID

(75) Inventor: Rafael Egger, München (DE)

(73) Assignee: LRE Medical GmbH, München (DE)

( * ) Notice: Subject to any disclaimer, the term of this patent is extended or adjusted under 35 U.S.C. 154(b) by 167 days.

(21) Appl. No.: 12/487,912

(22) Filed: Jun. 19, 2009

(65) Prior Publication Data
US 2009/0323070 A1   Dec. 31, 2009

(30) Foreign Application Priority Data
Jun. 25, 2008 (DE) .................. 10 2008 030 277

(51) Int. Cl.
*G01N 21/55* (2006.01)
(52) U.S. Cl. ........................................ 356/445; 356/448
(58) Field of Classification Search ........... 356/445–448
See application file for complete search history.

(56) References Cited

U.S. PATENT DOCUMENTS 5,449,898 A * 9/1995 Dosmann ................... 250/208.1
7,499,154 B2 * 3/2009 Stock et al. .................... 356/73

* cited by examiner

*Primary Examiner* — Michael P Stafira
(74) *Attorney, Agent, or Firm* — McCormick, Paulding & Huber LLP

(57) ABSTRACT

In a method for determining the concentration of at least one substance in a liquid the liquid is applied onto a test strip containing at least one test zone, wherein an optical sensor arrangement is moved step-by-step in a first direction over the surface of the test strip while the test trip is at the same time irradiated with light of a predetermined wave length and wherein in each step the radiation reflected from the surface of the test strip is measured, and wherein in each measurement step the test strip surface is irradiated alternately with light of at least two different wave lengths and the irradiation is measured at the same time and the difference between the measurement signals obtained in each measurement step using irradiation light of different wave lengths is analyzed.

7 Claims, 3 Drawing Sheets

METHOD AND APPARATUS FOR DETERMINING THE CONCENTRATION OF A SUBSTANCE IN A LIQUID

CROSS REFERENCE TO RELATED APPLICATION

This application claims the benefit of German Application No. 102008030277.5 filed Jun. 25, 2008, the disclosure of which is herein incorporated by reference in its entirety.

FIELD OF THE INVENTION

The invention relates to a method for determining the concentration of at least one substance in a liquid, wherein the liquid is applied onto a test strip containing at least one test zone and wherein an optical sensor arrangement is moved step-by-step in a first direction over the surface of the test strip while the test strip is irradiated with light of a predetermined wave-length and wherein during each step the radiation reflected from the surface of the test strip is measured.

BACKGROUND OF THE INVENTION

Usually test strips consist of an absorptive carrier material transporting the liquid to be examined, onto which carrier material one or more test zones have been applied, the test zones being, for example, shaped as lines and extending transversely across the width of the test strip and containing a reagent reacting with the substance to be detected in a detection assay, which assay usually consists in a change of the colour of the test zone and can therefore be measured optically. Moreover the test strip can be provided with a control zone situated in a spaced relationship behind the one or more test zones when viewed in the flow direction of the liquid to be examined. The control zone serves primarily to establish the progress of the wetting of the test strip by means of repeated amplitude measurements and to thereby trigger the start of the measuring action. If sufficient wetting is detected at the control zone it is after all safe to assume that the test zone located in front of the control zone in the flow direction has also been wetted sufficiently to provide a usable measuring signal. Moreover the measured values obtained at the control zone may also be used to determine the plausibility of the actual measurement results obtained at the test zone.

In actual practice it has been shown that the measurement curve obtained by moving the sensor arrangement over the test strip surface and at the same time measuring the reflected light also contains signals which are comparable with the actual measured signals in their amplitude but which are the results of disturbances, i.e. which are artefacts. Such artefacts may for instance occur when the measuring strip is covered with a transparent foil which causes undesired reflexes when irradiated with the measuring light. However artefacts may also be the result of impurities or inhomogenities in the measuring strip.

The invention has as its object to provide a method of the kind mentioned above which enables the detection of artefacts of the aforementioned kind in a simple manner.

SUMMARY OF THE INVENTION

According to the invention, this object is attained with a method of the kind mentioned above by irradiating the test strip surface in each measuring step alternately with light of at least two different wave lengths and at the same time measuring the reflected radiation, and by evaluating the difference in the measuring signals obtained in each measuring step with light of different wave lengths.

First it is to be pointed out that the light used for the irradiation of test strips does not only include visible light but that it can for instance also consist of infrared radiation. The invention is based on the realization that the measuring signals derived from disturbances are independent of wave length and therefore can be eliminated by differential calculation. Signals obtained from the test zones, on the contrary, differ noticeably when the test zones are irradiated with light of different wave lengths. In this manner it is therefore possible to recognize and mathematically exclude artefacts in the measurement curve.

When the sensor arrangement is a sensor line extending transversely to the first direction, i.e. to the scanning direction, it is possible to calculate a mean value from the differential signals obtained in each measuring step by a plurality of sensors in the sensor line. At least in the case of local disturbances which do not extend over the entire width of the test strip sensors located next to each other in the sensor line will deliver different measurement results. By calculating a mean value the disturbance is then 'levelled out' so to speak. What is to be expected, however, is that all sensors in the test zone deliver the same measured value over the entire width of the test strip. This also makes it possible to detect artefacts in the measurement curve.

The invention further concerns an apparatus for determining the concentration of at least one substance in a liquid, which apparatus comprises a fixture for a test strip containing at least one test zone, at least one light source for illuminating the test strip surface, an optical sensor arrangement for detecting the light reflected from the test strip surface, and an analyzing unit linked to the sensor arrangement and used for analyzing the measured signals provided by the sensor arrangement, the sensor arrangement being moveable step-by-step in a first direction over the test strip fixture. According to the invention at least two light sources are provided which deliver light of different wave lengths, the apparatus being controllable in such a manner that in each measurement step the test strip surface is illuminated alternately with light from the two light sources and the reflected light is measured simultaneously.

Preferably the sensor arrangement contains a line sensor which is arranged transversely to the first direction.

BRIEF DESCRIPTION OF THE DRAWINGS

The following description in conjunction with the accompanying drawings explains the invention by means of an exemplary embodiment. In the drawings

DESCRIPTION OF THE PREFERRED EMBODIMENTS

Figure 1:
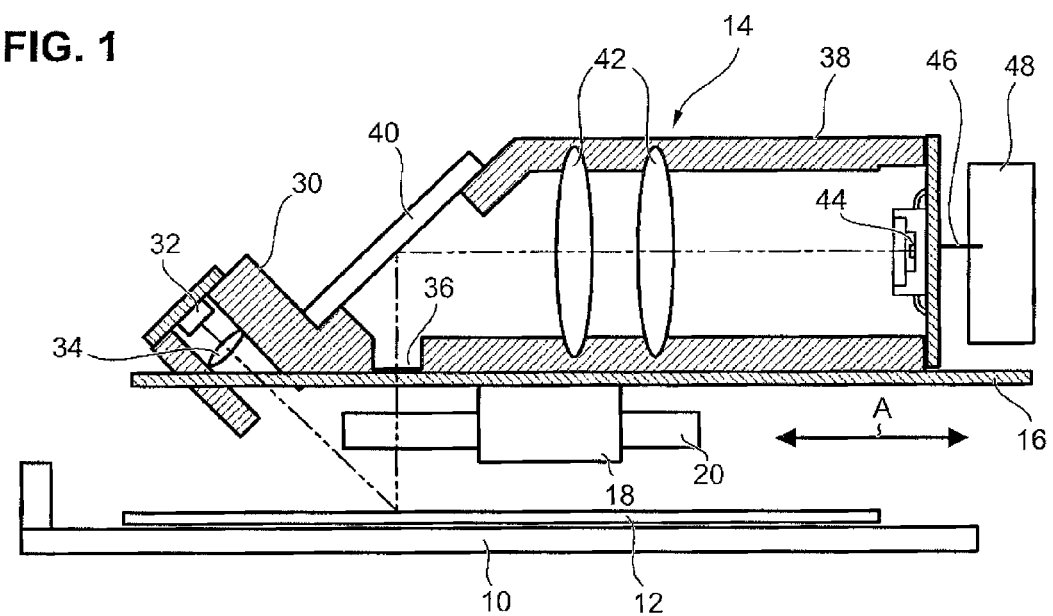
FIG. 1 shows a schematic side view of an arrangement for scanning a test strip.
Figure 2:
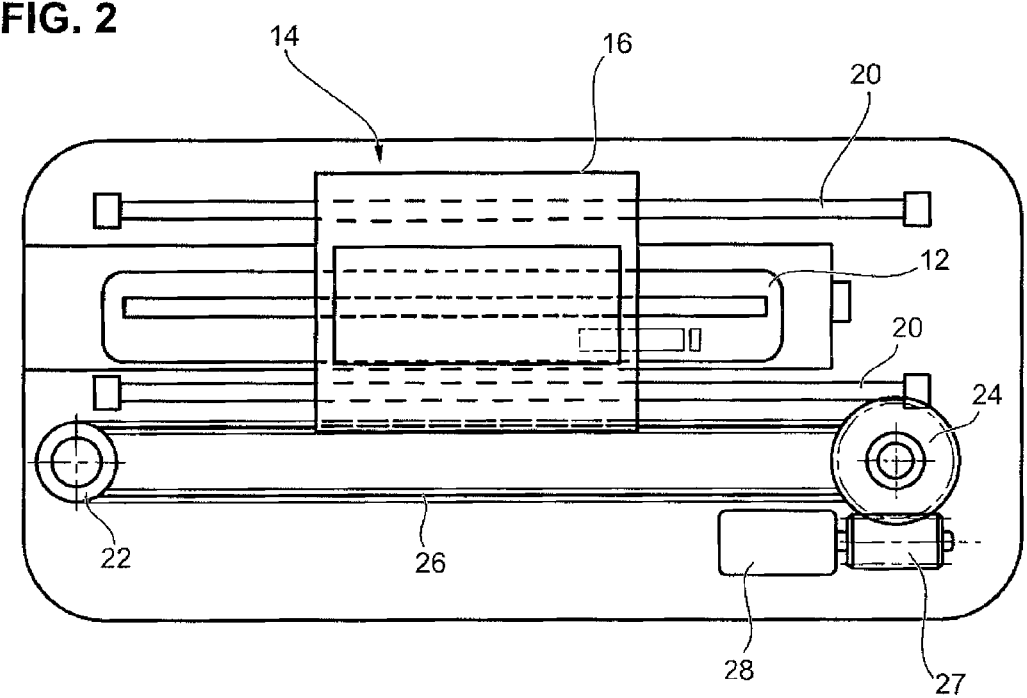
FIG. 2 shows a schematic plan view onto the arrangement depicted in FIG. 1.

In FIGS. 1 and 2 only the most important parts of the apparatus according to the invention are shown schematically. Reference numeral 10 denotes a fixture for a test strip 12. Above the fixture an optical measurement system 14 is located which comprises a base plate or platform 16, which, by means of two guides 18, can be reciprocated on two parallel rails 20 over the surface of the fixture 10 or the test strip 12, respectively, in the direction of the double arrow A in FIG. 1. For this purpose a drive is provided with a belt 26 guided over two rollers 22, 24, which belt is fixed to the platform 16, the roller 24 being driveable via a screw drive 27 and a step motor 28 (FIG. 2).

The measuring system 14 comprises a first housing part 30, in which two LEDs are located, which in the drawing are depicted jointly as a single block 32. One of these LEDs delivers for example green light ($\lambda$=520 nm) and the other one delivers infrared radiation ($\lambda$=740 nm). The light of these LEDs is directed by means of an optical system 34 onto the test strip 12 in such a manner that a rectangular illumination field is formed. The light reflected from the test strip 12 enters through an aperture 36 into a second housing part 38 and is imaged via a mirror 40 and an imaging optical system 42 onto a line sensor 44 which is connected via a line 46 to an analyzing unit 48.

Figure 3:
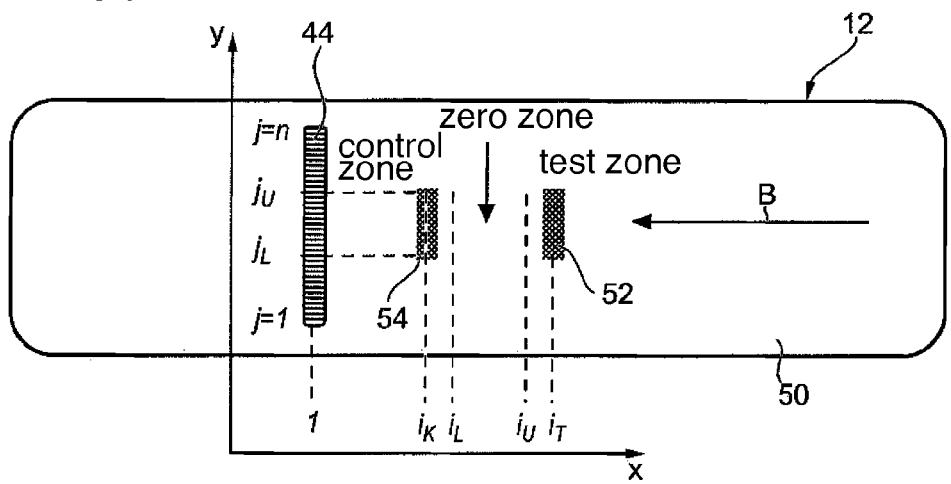
FIG. 3 shows a schematic depiction of a test strip.

FIG. 3 shows in a schematic depiction the basic elements of a test strip. This test strip 12 normally includes an elongated carrier 50, onto which at least one test zone 52 is applied in a spaced relationship to one end of the carrier, and onto which a control zone 54 is applied in a spaced relationship to the test zone. The test zone contains a reagent which reacts with the substance to be detected, the reaction causing, for example, a colour change which means that the reflectivity of the test zone changes when the substance to be detected is present. The liquid to be examined is applied to the right of the test zone 52 in FIG. 3 and flows due to the capillary action in the carrier material in the direction of the arrow B through the test strip thus reaching first test zone 52 and subsequently control zone 54. Therefore, if a wetting of the test strip 12 by the liquid to be examined can be detected in control zone 54, it is safe to assume that also the test zone 52 has been wetted sufficiently by the liquid to be examined.

In FIG. 3 the X-axis depicts the direction of the relative movement between the test strip 12 and the optical measuring system 14 and the single movements and measurements steps are denoted by 1 ... i .... Moreover the location of the sensor line 44 is shown schematically, the longitudinal line direction of which extends transversely to the longitudinal direction of the test strip, i.e. in the Y-direction, and the respective positions of the single sensors (image points) are denoted by the numbers 1 ... j ....

Figure 4:
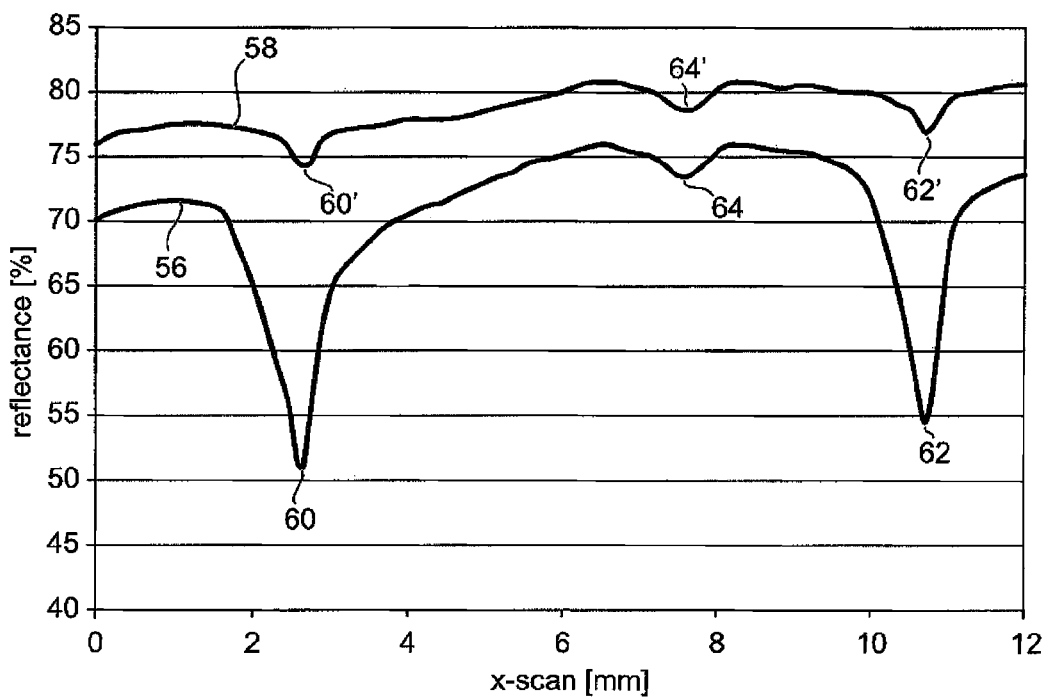
FIG. 4 shows a measurement diagram for explaining the method according to the invention depicting the reflectance curves obtained with measuring light of two different wavelengths.

If the measuring system 14 together with the sensor arrangement 44 is moved in the direction of the X-axis, i.e. in the direction of the double arrow A in FIG. 1, relatively to the test strip 12, the measurement curves shown in FIG. 4 are obtained for a single sensor within the sensor line 44, whereby in each movement step (X position) a measurement is made during illumination both with the green LED and the infrared LED. The measurement curve 56 consists of measurement points obtained with green light and the curve 58 consists of measurement points obtained with infrared light.

In FIG. 4 both at the location of the control zone and at the location of the test zone a clear reflectance minimum 60 and 62, respectively, can be seen in the measurement curve obtained for the green light and a reflectance minimum 60' and 62', respectively, which is not so clearly defined, can be seen in the measurement curve obtained for the infrared radiation. Between the two minima 60 and 62 a further minimum 64 is located which is at least approximately the same for the two measurement curves and which is caused by a disturbance. Such disturbances may be caused by contamination or deformation of the test strip. Depending on the quality, grade and treatment of the test strip surface, such disturbances can occur any number of times and their strength and location can not be predicted. In many cases, as in the case depicted in the drawings, the influence of a disturbance on the reflectance is not dependent on wave length. This provides the opportunity to detect and eliminate the disturbances.

At the same time the area located between the signals of the control zone and those of the test zone allows the determination of a base line, which can be used as a reference line for the assessment of the test zone amplitude and of the area $\alpha$, respectively, which area is defined by the signal envelope. During the measuring of an internal standard of an apparatus for each image point j corresponding to each single sensor within the sensor line the coefficients $c_j^G$ (G for green) and $C_j^{IR}$ (IR for infrared) are stored. These coefficients $c_j$ serve to convert the counted measurands $EC_j$ of the detector into reflectance percents. After a test strip has been scanned the image points obtained under green light are subtracted from the image points obtained under infrared light and absorption curves are obtained for all image points j.

In the formula (1) for the reflectance difference $a_{ji}$ $$a_{ji} = \frac{EC_j^{IR}}{c_j^{IR}} - \frac{EC_j^G}{c_j^G} \qquad (1)$$

the coefficients $c_j^{IR}$ are substituted by the predefined coefficients $c_j^G$. The mean value of all relevant image points $j_L \ldots j_U$ in the area of the base line (X-positions $i_L \ldots i_U$) is obtained using formula (2).

$$A_j = \frac{1}{i_u - i_L} \sum_{i_u - i_L} a_{ij} \qquad (2)$$

Figure 5:
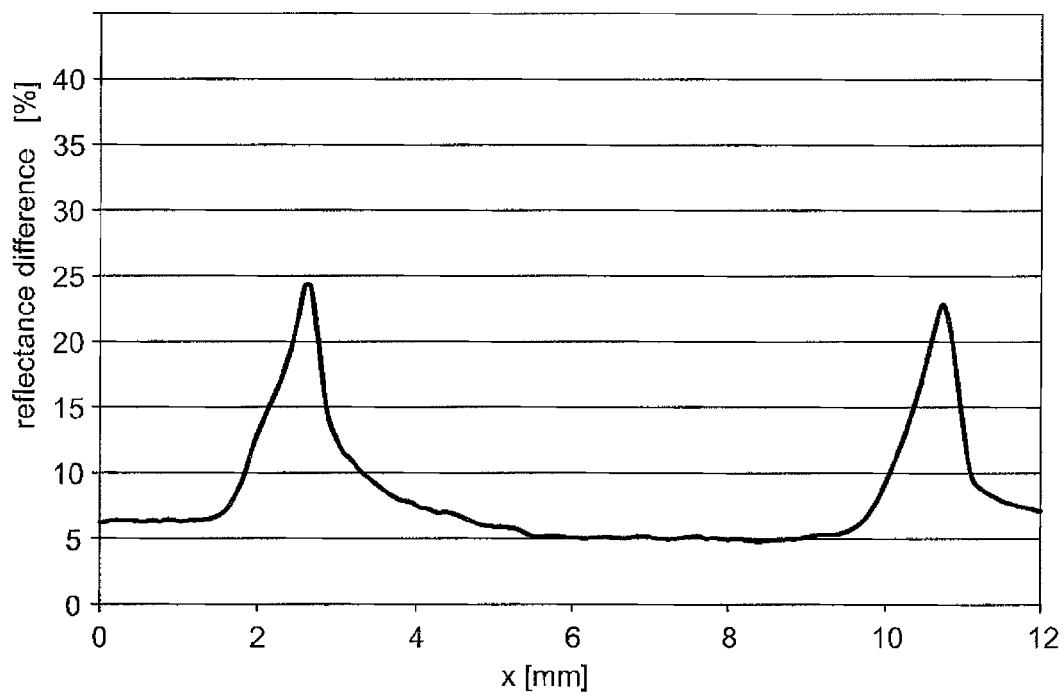
FIG. 5 shows a depiction of the difference of the two reflectance curves shown in FIG. 4.

The signal characteristics after calculating the difference and the mean value are shown in FIG. 5. As can be seen, the disturbance between the control zone signal and the test zone signal has disappeared. The base line located between the two peaks of the difference curve serves as a reference line for the analysis of the amplitudes and the surface areas of the peaks of the difference curves.

What is claimed is:
1. A method for determining the concentration of at least one substance in a liquid, the method comprising the following steps:
   applying the liquid onto a test strip containing at least one test zone;
   moving an optical sensor arrangement step-by-step in a first direction relative to the surface of the test strip;
   irradiating the test trip during the step of moving with light of two different wave lengths;
   measuring the radiation reflected from the surface of the test strip by the two different wave lengths during the step of moving to determine a first measurement curve representing radiation reflected by the light of one wave length and a second measurement curve representing radiation reflected by the light of the other wave length; and
   analyzing the difference between the first measurement curve and the second measurement curve to exclude artefacts from the measurement curves.

2. The method according to claim 1, wherein the sensor arrangement is a sensor line having a plurality of sensors extending transversely to the first direction and that a mean value is formed out of the different curves obtained by the plurality of sensors contained in the sensor line in each measurement step.

3. The method according to claim 1, wherein the test strip contains in addition to the test zone a control zone located in a spaced relationship to the test zone.

4. An apparatus for determining the concentration of at least one substance in a liquid, the apparatus comprising:
- a fixture configured to hold a test strip containing at least one test zone;
- at least two light sources providing light of different wave lengths for irradiating the test strip surface, the two light sources being controllable in such a manner that the test strip surface is irradiated alternately with light from each of the light sources;
- an optical sensor arrangement being moveable step-by-step in a first direction relative to the surface of the fixture for detecting the light reflected from the test strip surface by each of the light sources to provide a measurement signal for each of the light sources; and
- an analyzing unit connected to the optical sensor arrangement for analyzing the measurement signals provided by the optical sensor arrangement by each of the light sources, the analyzing unit comparing the measurement signals to each other and providing a difference curve.

5. The apparatus according to claim 4, wherein the optical sensor arrangement contains a line sensor arranged transversely to the first direction.

6. The apparatus according to claim 4, wherein the analyzing unit is programmed so that a mean value is formed from the different signals being obtained in each measurement step by a plurality of sensors of the sensor line.

7. The apparatus according to claim 4, wherein the test strip contains a control zone in addition to the test zone.

* * * * *